United States Patent [19]

Swearingen et al.

[11] Patent Number: 4,701,529

[45] Date of Patent: Oct. 20, 1987

[54] SINGLE PASS PROCESS FOR MAKING TRIMETHYL PYRIDINE

[75] Inventors: Loren L. Swearingen, Irving; Wallace E. Embrey, Freeport; Randy J. LaTulip; Jim D. Earls, both of Lake Jackson, all of Tex.; Garnet E. McConchie, Stade, Fed. Rep. of Germany

[73] Assignee: The Dow Chemical Company, Midland, Mich.

[21] Appl. No.: 916,772

[22] Filed: Oct. 9, 1986

Related U.S. Application Data

[63] Continuation-in-part of Ser. No. 793,890, Nov. 1, 1985, abandoned.

[51] Int. Cl.$^4$ ............................................... C07D 213/9
[52] U.S. Cl. ..................................... 546/251; 546/250
[58] Field of Search ................................ 546/250, 251

[56] References Cited

U.S. PATENT DOCUMENTS

| | | | |
|---|---|---|---|
| 3,781,292 | 12/1973 | Kusonoki et al. | 546/253 |
| 3,829,429 | 8/1974 | Clement | 546/253 |
| 4,140,690 | 2/1979 | Dolhyj et al. | 546/253 |
| 4,220,783 | 9/1980 | Chang et al. | 546/251 |

OTHER PUBLICATIONS

Avots et al., Chem. Abstracts, vol. 80, (3), Abst. No. 80:14821g (Jan. 21, 1974).

Cerny, Chem. Abstracts, vol. 91(3), Abst. No. 91:20268a, Jul. 16, 1979.

*Primary Examiner*—Alan L. Rotman
*Attorney, Agent, or Firm*—B. G. Colley

[57] ABSTRACT

Process for the production of 2,4,6-trimethyl pyridine wherein acetone or an acetone derivative is reacted under pressure with ammonia in the presence of a metallic catalyst to form mixture of products with a high preparation of 2,4,6-trimethyl pyridine and recovering the trimethyl pyridine.

7 Claims, No Drawings

4,701,529

SINGLE PASS PROCESS FOR MAKING TRIMETHYL PYRIDINE

CROSS REFERENCE TO RELATED APPLICATION

This application is a continuation-in-part of Ser. No. 793,890 filed Nov. 1, 1985, now abandoned.

BACKGROUND OF THE INVENTION

This invention is a process for the production of 2,4,6-trimethyl pyridine wherein acetone or an acetone derivative is reacted with ammonia or aqueous solutions thereof to form a mixture containing 2,4,6-trimethyl pyridine. The mixture is then treated to recover 2,4,6-trimethyl pyridine in high yields.

Technical grade collidine or 2,4,6-trimethyl pyridine (TMP) is commercially available as a coal tar extract and contains a mixture of trimethyl and dimethyl pyridines which are difficult to separate due to their close boiling points.

There are many known synthetic methods to make 2,4,6-trimethyl pyridine as is illustrated by U.S. Pat. Nos. 3,781,292; 3,829,429, 4,140,690, and 4,220,783.

It is known from U.S. Pat. No. 2,796,421 to react ketones and ammonia over a catalyst to make trimethyl pyridines. However, this single pass process over silica-alumina gives low yields as is shown by the control set forth herein.

SUMMARY OF THE INVENTION

It now has been discovered that 2,4,6-trimethyl pyridine can be made in high yields and high purity by a process wherein acetone or an acetone derivative can be reacted with ammonia at a relatively high temperature to make a crude mixture of products containing 2,4,6-trimethyl pyridine which is then purified and 2,4,6-trimethyl pyridine is isolated.

The essential steps in the process of this invention are:

(A) reacting acetone or an acetone derivative with ammonia in the presence of an inorganic dehydrogenation catalyst containing one or more metals from Groups IVB to VIII of the Periodic Table or their compounds at a temperature in the range from about 300° to about 475° C. under a pressure in the range from about 2 to about 50 atmospheres with a liquid hourly space velocity 0.01 reciprocal hours and a mole ratio of ammonia to acetone or acetone derivatives equal to or greater than 0.2:1 to form a mixture of products containing a high proportion of TMP and (B) recovering TMP from said mixture.

DETAILED DESCRIPTION OF THE INVENTION

In the process of this invention acetone is reacted with ammonia. While acetone is the preferred starting material, other compounds such as mesityl oxide and diacetone alcohol can be used.

The process is carried out with an ammonia to acetone or acetone derivative mole ratio in the range 0.2:1 to 14:1 with the preferred range being 4:1 to 8:1. Higher mole ratios give no advantage while lower mole ratios lead to decreased yields of trimethyl pyridine.

The temperature should be in the range from 300° to 475° C. and the preferred range is 360° to 390° C.

The liquid hourly space velocity of the reactants through the catalyst should be in the range 0.01 to 5.0 reciprocal hours and preferably in the range 0.2 to 2.0.

The pressure range should be in the range from about 2 to about 50 atmospheres.

The reaction product of the reaction is recovered and purified. The light products i.e. acetone, ammonia, acetone imine, mesityl oxide and mesityl imine can be flashed off and recycled to the reactor. The remainder can be distilled preferably under a nitrogen atmosphere and under a sub-atmospheric pressure of approximately 100 mm Hg and a temperature range from 45° to 140° C.

Examples of catalysts useful herein are activated alumina, silica-alumina or activated zeolite substrates impregnated with catalytic material processing relatively high dehydrogenation activity or properties. In general, the appropriate dehydrogenation catalytic material within the scope of this invention include the Group IVB to Group VIII metals of the Periodic Table. Still another group of these dehydrogenation materials comprise the oxides, halides, sulfides, selenides, molybdates, chromates, and manganates, of the above class of metals.

Any one or a plurality of the above metal or metal compounds possessing dehydrogenation activity may be used in admixture or as a deposit on the surface of the activated alumina, silica-alumina, or activated zeolite catalysts.

The preferred dehydrogenation materials for use in the scope of this invention include any one or a plurality of the following metals or their oxides: nickel, molybdenum, cobalt, tungsten, rhodium, rhenium, palladium, and platinum.

The following examples and controls are presented to further illustrate, but not limit the invention set forth in the claims.

EXAMPLE 1

Acetone was reacted with ammonia to produce 2,4,6 trimethylpyridine in a single-pass, fixed bed reactor (1" diameter). The reactor held 250 ml of catalyst and ammonia and acetone were fed into the top of the reactor via separate lines. The product exiting the reactor was condensed in a stainless steel watercooled heat exchanger. Samples were analyzed by gas chromotography and H$_2$O analyses were performed using the Karl Fischer titration technique. Acetone was passed over 6.7% NiO/27.0% MoO$_3$ on an alumina based catalyst at a rate of 1 ml/min (0.24 hr$^{-1}$LHSV). A 4/1 ammonia/acetone molar ratio was maintained while operating at 65 psig and 350° C. A sample of the reactor product gave the following results:

| Product | Weight % |
| --- | --- |
| 2,4,6-TMP | 25.2 |
| Acetone | 8.6 |
| Unknown Lights | 13.7 |
| Mesityl Oxide | 0.6 |
| Mesitylene | 13.8 |
| Picoline | 1.1 |
| Acetonin | 0.7 |
| Diacetone Alcohol | 1.4 |
| Phorone | 0.4 |
| Isophorone | 0.1 |
| Unknown Heavies | 18.4 |
| H$_2$O | 16.0 |
| % Yield to 2,4,6-TMP | 39.7 |
| Based on consumed acetone | |

-continued

| Product | Weight % |
| --- | --- |
| % Acetone Conversion | 91.4 |

EXAMPLE 2

Utilizing the same equipment mentioned in Example 1, the ammonia/acetone reaction was conducted using 0.5% palladium oxide on alumina catalyst under the following conditions and resulting in the following products:

| | |
| --- | --- |
| Temperature °C. | 379 |
| Pressure psig | 89 |
| LHSV hr$^{-1}$ | 0.13 |
| NH$_3$/Acetone mole ratio | 7:1 |

| Product | Weight % |
| --- | --- |
| 2,4,6-TMP | 18.2 |
| Acetone | 27.5 |
| Unknown Lights | 8.3 |
| Mestyl Oxide | 1.7 |
| Mesitylene | 0.7 |
| Tetrapyre | 2.9 |
| Acetonin | 13.1 |
| Isophorone | 8.7 |
| Unknown Heavies | 4.9 |
| Water | 14.0 |
| % Yield to 2,4,6-TMP Based on consumed acetone | 36.1 |
| % Acetone Conversion | 72.5 |

EXAMPLE 3

Utilizing the same equipment mentioned in Example 1 the ammonia/acetone reaction was conducted using 0.5% palladium oxide on alumina catalyst under the following conditions and resulting in the following products:

| | |
| --- | --- |
| Temperature °C. | 378 |
| Pressure psig | 56 |
| LHSV hr$^{-1}$ | 0.27 |
| NH$_3$/Acetone mole ratio | 4:1 |

| Product | Weight % |
| --- | --- |
| 2,4,6-TMP | 16.4 |
| Acetone | 38.4 |
| Unknown Lights | 0.2 |
| Mestyl Oxide | 1.0 |
| Mesitylene | 0.3 |
| Tetrapyre | 0.1 |
| Acetonin | 21.9 |
| Diacetone Alcohol | 2.5 |
| Picoline | 0.1 |
| Isophorone | 4.7 |
| Unknown Heavies | 5.4 |
| Water | 9.0 |
| % Yield to 2,4,6-TMP Based on consumed acetone | 38.3 |
| % Acetone Conversion | 61.6 |

EXAMPLE 4

Ammonia and acetone were also reacted over a 0.3% platinum/alumina catalyst utilizing the same equipment mentioned in Example 1. The following conditions were used resulting in the following products:

| | |
| --- | --- |
| Temperature °C. | 375 |
| LHSV hr$^{-1}$ | 0.24 |
| NH$_3$/Acetone mole ratio | 4:1 |
| Pressure psig | 95 |

| Product | Weight % |
| --- | --- |
| 2,4,6-TMP | 15.7 |
| Acetone | 40.2 |
| Unknown Lights | 8.5 |
| Mesityl Oxide | 2.1 |
| Mesitylene | 0.8 |
| Tetrapyre | 0.6 |
| Acetonin | 3.0 |
| Isophorone | 5.5 |
| Unknown Heavies | 8.5 |
| H$_2$O | 15.0 |
| % Yield to 2,4,6-TMP Based on consumed acetone | 37.7 |
| % Acetone Conversion | 59.8 |

Control 1

An ammonia/acetone reaction was run over a SiO$_2$/Al$_2$O$_3$ catalyst in order to reproduce the prior state-of-the-art process which is shown in U.S. Pat. No. 2,796,421. The following conditions were used resulting in the following products:

| | |
| --- | --- |
| Temperature °C. | 360 |
| Pressure psig | 45 |
| LHSV hr$^{-1}$ | 0.24 |
| NH$_3$/Acetone mole ratio | 4:1 |

| Product | Weight % |
| --- | --- |
| 2,4,6-TMP | 14.3 |
| Acetone | 14.4 |
| Lights | 5.7 |
| Mesityl Oxide | 0.7 |
| Mesitylene | 8.0 |
| Tetrapyre | 1.3 |
| Acetonin | 1.1 |
| Diacetone Alcohol | 0.3 |
| *Isophorone | 9.6 |
| *Unknown Heavies | 29.6 |
| H$_2$O | 15.0 |
| % Yield to 2,4,6-TMP Based on consumed acetone | 24.0 |
| % Acetone Conversion | 85.6 |

Large losses to unrecyclable heavies and isophorone.

We claim:

1. A method for the preparation of 2,4,6 trimethylpyridine (TMP) which comprises
   (A) reacting a member of the group consisting of acetone, mesityl oxide, and diacetone alcohol with ammonia in the presence of an inorganic dehydrogenation catalyst containing one of more metals from Groups IVB to VIII of the Periodic Table or their compounds selected from the group consisting of oxides, halides, sulfides, selenides, molybdates, chromates, and manganates at a temperature in the range from about 300° to about 475° C. under a pressure in the range from about 2 to about 50 atmospheres with a liquid hourly space velocity from 0.01 to 50 reciprocal hours and a mole ratio of ammonia to said above group member equal to or greater than 0.2:1 to form a mixture of products containing a high proportion of TMP and (B) recovering TMP from said mixture.

2. The method of claim 1 wherein said metals are selected from the group consisting of platinum, palladium, nickel, cobalt, rhodium, tungsten, molybdenum and rhenium.

3. The method of claim 2 wherein the metals are used in their oxide form.

4. The method as set forth in claim 1 wherein the process is conducted with a liquid hourly space velocity in the range from 0.01 to 5.0 reciprocal hours and with a mol ratio of ammonia to acetone or acetone derivatives in range from 0.2:1 to 14:1.

5. A method for the preparation of 2,4,6-trimethylpyridine (TMP) which comprises (A) reacting a member of the group consisting of acetone, mesityl oxide, and diacetone alcohol with ammonia in the presence of an inorganic catalyst containing one or more metals selected from the group consisting of platinum, palladium, nickel, cobalt, rhodium, tungsten, molybdenum and rhenium or their oxides at a temperature in the range from about 360° to about 390° C. under a pressure in the range from 2 to 50 atmospheres with a liquid hourly space velocity in the range from 0.2 to 2.0 reciprocal hours and a mol ratio of ammonia to said above group member in the range from 4:1 to 8:1 to form a mixture of products containing a high proportion of TMP and (B) recovering TMP from said mixture.

6. The process as set forth in claim 5 wherein anhydrous ammonia is reacted with acetone.

7. The process as set forth in claim 5 wherein the catalysts are supported on alumina, silica-alumina, silica-magnesia, or silica-alumina-magnesia supports.

* * * * *